(12) United States Patent
Belfadhel et al.

(10) Patent No.: US 8,034,967 B2
(45) Date of Patent: Oct. 11, 2011

(54) METHOD OF PREPARING A PURIFIED ESTER-SUBSTITUTED PHENOL STREAM

(75) Inventors: Hatem Belfadhel, Roosendaal (NL); Stephan Bouwens, Bergen op Zoom (NL); Martin Herke Oyevaar, Goes (NL)

(73) Assignee: Sabic Innnovative Plastics IP B.V., Bergen op Zoom (NL)

( * ) Notice: Subject to any disclaimer, the term of this patent is extended or adjusted under 35 U.S.C. 154(b) by 957 days.

(21) Appl. No.: 11/948,063

(22) Filed: Nov. 30, 2007

(65) Prior Publication Data

US 2009/0143610 A1 Jun. 4, 2009

(51) Int. Cl.
*C07C 67/48* (2006.01)
*C07C 68/02* (2006.01)
*C08G 64/20* (2006.01)
*C08G 64/30* (2006.01)

(52) U.S. Cl. ............ 558/274; 558/271; 560/64; 560/67; 560/71

(58) Field of Classification Search .................. None
See application file for complete search history.

(56) References Cited

U.S. PATENT DOCUMENTS

| | | | | |
|---|---|---|---|---|
| 3,470,133 | A * | 9/1969 | Ohme | .......................... 528/490 |
| 3,939,153 | A | 2/1976 | Fowler | |
| 4,323,668 | A | 4/1982 | Brunelle | |
| 4,457,807 | A | 7/1984 | Rulkens et al. | |
| 4,566,947 | A | 1/1986 | Tsuruta | |
| 6,576,119 | B2 | 6/2003 | Ishida et al. | |
| 6,790,929 | B2 * | 9/2004 | Silvi et al. | ..................... 528/198 |
| 2005/0234211 | A1 | 10/2005 | Martinez et al. | |
| 2006/0025622 | A1 | 2/2006 | Buckley et al. | |
| 2006/0069228 | A1 | 3/2006 | McCloskey et al. | |
| 2006/0094856 | A1 | 5/2006 | Hidalgo et al. | |
| 2007/0282091 | A1 | 12/2007 | Buckley et al. | |

FOREIGN PATENT DOCUMENTS

WO    2007143319 A1    12/2007

OTHER PUBLICATIONS

Masanori et al., "Manufacture of polycarbonates with discoloration prevention by melt polymerization", CAPLUS, Jan. 1, 1900, XP002456157.

* cited by examiner

*Primary Examiner* — Daniel Sullivan
*Assistant Examiner* — Yevegeny Valenrod
(74) *Attorney, Agent, or Firm* — Larson & Anderson, LLC

(57) ABSTRACT

A method of producing a purified ester-substituted phenol stream is provided. The method includes a first step of obtaining from a melt transesterification reaction a byproduct stream containing a residual ester-substituted diaryl carbonate, an ester-substituted phenol, a residual melt transesterification catalyst, and a catalyst degradation product. A second step includes treating the reaction byproduct stream to separate ester-substituted phenol and catalyst degradation product from residual ester-substituted diaryl carbonate and residual melt transesterification catalyst to create a light recycle stream containing ester-substituted phenol and catalyst degradation product and a heavy recycle stream containing residual ester-substituted diaryl carbonate and residual melt transesterification catalyst. A third step includes treating the light recycle stream to reduce catalyst degradation product concentration thereby producing a purified ester-substituted phenol stream.

20 Claims, 6 Drawing Sheets

METHOD OF PREPARING A PURIFIED ESTER-SUBSTITUTED PHENOL STREAM

BACKGROUND

Ester-substituted diaryl carbonates such as bismethylsalicylcarbonate (BMSC) have proven to be useful starting materials in the preparation of polycarbonates via the melt reaction of a diaryl carbonate with dihydroxy compounds. See for example, U.S. Pat. No. 4,323,668 in which rates of polymerization of BMSC with bisphenol A were shown to be higher than the corresponding rates of polymerization of bisphenol A with an unsubstituted diaryl carbonate, such as diphenyl carbonate. The product polycarbonate formed using ester-substituted carbonates, such as BMSC, contain high amounts of reaction byproducts such as ester-substituted phenols (e.g. methyl salicylate (MS)), inter alia, that are often removed prior to achieving a finished polycarbonate product. In order to achieve high efficiencies and to decrease amounts of unusable waste byproducts generated by polycarbonate production facilities, it would be desirable to find a use for the removed byproducts. The present invention provides a method of purifying the byproduct stream and making ester-substituted diaryl carbonates using the byproduct ester-substituted phenol.

SUMMARY OF INVENTION

In one embodiment, the present invention provides a method of producing a purified ester-substituted phenol stream from a melt transesterification reaction byproduct stream, the method comprising the sequential steps of:
  (a) obtaining from a melt transesterification reaction a byproduct stream comprising a residual ester-substituted diaryl carbonate, an ester-substituted phenol, a residual melt transesterification catalyst, and a catalyst degradation product,
    wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and
    wherein the catalyst degradation product comprises a trialkyl phosphine, a trialkyl amine, or both,
  (b) treating the byproduct stream to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and
  (c) treating the light recycle stream to reduce catalyst degradation product concentration,
  thereby producing a purified ester-substituted phenol stream.

In another embodiment the present invention provides a method of producing a purified ester-substituted phenol stream from a melt transesterification reaction byproduct stream, the method comprising the sequential steps of:
  (a) obtaining from a melt transesterification reaction a byproduct stream comprising a residual ester-substituted diaryl carbonate, an ester-substituted phenol, a residual melt transesterification catalyst, and a catalyst degradation product,
    wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and
    wherein the catalyst degradation product comprises a trialkyl phosphine, a trialkyl amine, or both,
  (b) introducing the byproduct stream to a first rectification column operating under conditions to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and
  (c) introducing the light recycle stream to a second rectification column operating under conditions to separate catalyst degradation product from ester-substituted phenol, thereby creating a catalyst degradation product stream and a purified ester-substituted phenol stream, wherein the ester-substituted phenol stream has less than 1.00 ppm catalyst degradation product present.

In a further embodiment the present invention provides a method of producing an ester-substituted diaryl carbonate from a purified ester-substituted phenol stream from a melt transesterification reaction byproduct stream, the method comprising the sequential steps of:
  (a) obtaining from a melt transesterification reaction a byproduct stream comprising a residual ester-substituted diaryl carbonate, an ester-substituted phenol, a residual melt transesterification catalyst, and a catalyst degradation product,
    wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and
    wherein the catalyst degradation product comprises a trialkyl phosphine, a trialkyl amine, or both,
  (b) introducing the byproduct stream to a first rectification column operating under conditions to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and
  (c) introducing the light recycle stream to a second rectification column operating under conditions to separate catalyst degradation product from ester-substituted phenol, thereby creating a catalyst degradation product stream and a purified ester-substituted phenol stream, wherein the ester-substituted phenol stream has less than 1.00 ppm catalyst degradation product present,
  (d) contacting the ester-substituted phenol stream with phosgene under conditions sufficient to form ester-substituted diaryl carbonate,
  thereby forming ester-substituted diaryl carbonate.

DETAILED DESCRIPTION

Figure 1:
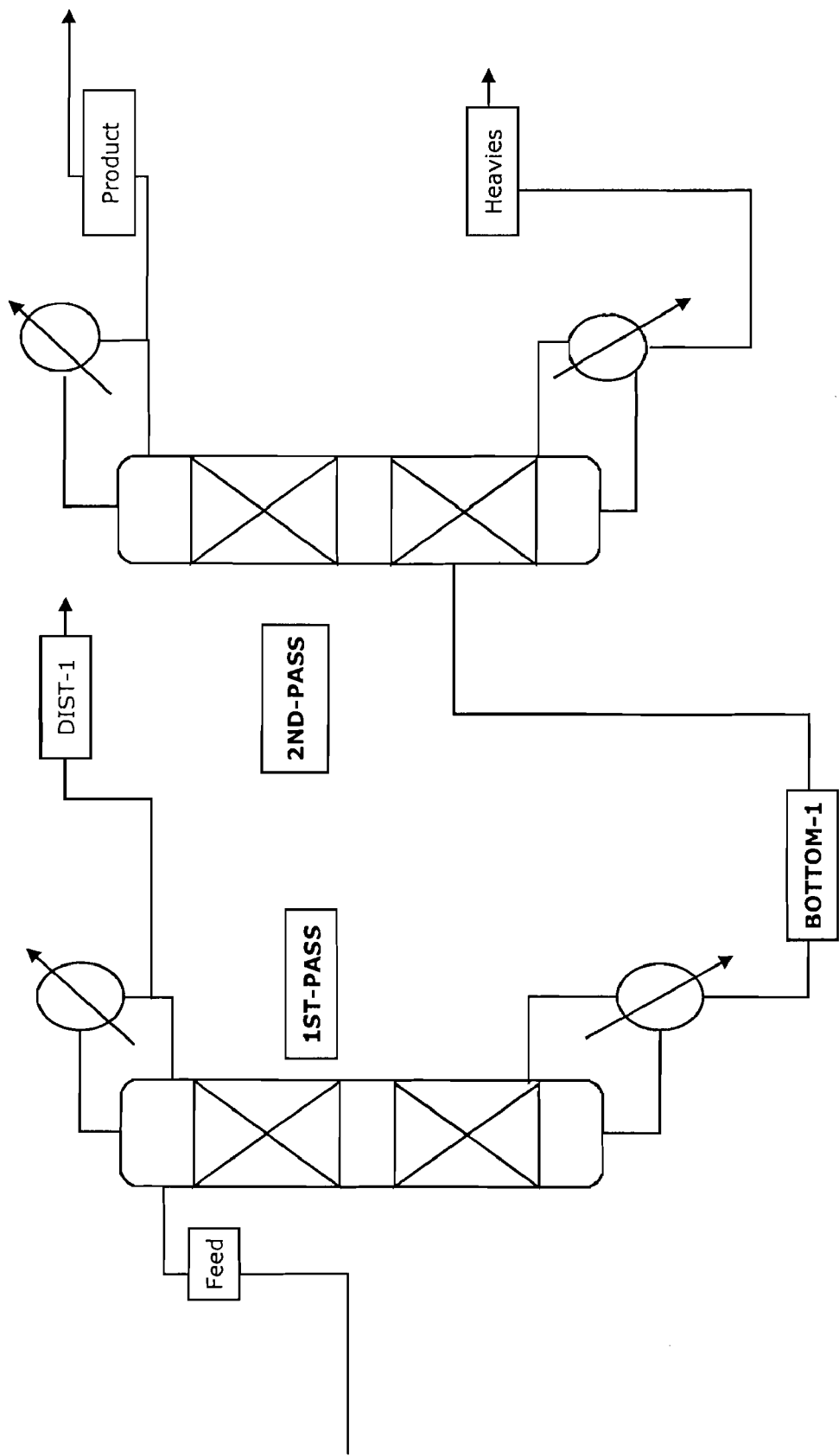
FIGS. 1-3 and 5 are block diagrams showing separation designs from the example section.

The melt production of polycarbonate, or polycarbonate oligomers, using an ester-substituted diaryl carbonate results in several byproducts including ester-substituted phenols. In order to achieve high plant efficiencies it is desirable that such byproducts be recycled to form, or reform, ester-substituted diaryl carbonates that are suitable for use, or reuse, in the melt production facility. This approach has the benefit of reducing the amount of byproduct waste generated during polycarbonate production while streamlining and reducing costs incurred by melt polycarbonate production facilities.

The production of ester-substituted diaryl carbonates using ester-substituted phenols is preferably achieved in the presence of an ethyl amine or ethyl phosphine catalyst, for example triethyl amine or triethyl phosphine. It would be expected that a trialkyl amine, or trialkyl phosphine, degradation product of which at least one of the alkyl groups is a methyl group would aid in, or at least not hinder, the promotion of such a reaction. However, it has been found that trialkyl amine and trialkyl phosphine catalyst degradation products which have at least one of methyl group (e.g. trimethyl amine, dimethylethyl amine, diethylmethyl amine, trimethyl phosphine, dimethylethyl phosphine, and/or diethylmethyl phosphine), if present, in an ester-substituted phenol leads to poor conversion of such into ester-substituted diaryl carbonate, thereby requiring the use of excess phosgene to reach higher conversions.

Furthermore, in recycle streams coming from melt polymerization reactions to form polycarbonate, residual dihydroxy monomer compositions and their degradation products may be present. It has been found that these compounds also lead to poor conversion of the ester-substituted phenol into ester-substituted diaryl carbonate.

As detailed in U.S. patent application Ser. No. 11/421,359 filed on May 31, 2006 which is herein incorporated by reference for all purposes, in order to achieve a high conversion of recycled ester-substituted phenols into ester-substituted diaryl carbonates, without the use of excessive amounts of phosgene, it has been found that the level of catalyst degradation products (trialkyl amines and trialkyl phosphines, that have at least one methyl group), should be reduced in the recycle byproduct ester-substituted phenol stream prior to the formation reaction of the ester-substituted diaryl carbonate. Furthermore, if residual dihydroxy monomer compounds and/or their degradation products are present they should also be removed.

It has now been found that certain processes for the purification of the recycle stream actually lead to the formation of additional catalyst degradation product and other byproducts that are undesirable in the purified ester-substituted phenol stream. The present invention provides a solution to this problem that includes a multi-stage separation method for the purification of the recycle stream. This process removes residual melt transesterification catalyst and other high boiling impurities (such as residual dihydroxy monomer compounds) in a first step prior to subsequent refinement of the stream.

In a preferred embodiment, this multi-stage separation/purification method is accomplished using a first and a second rectification column. The first rectification column operates under conditions to produce a lights top stream comprising catalyst degradation product and ester-substituted phenol and a heavies bottom product stream comprising residual catalyst and residual ester-substituted diaryl carbonate. The lights stream is subsequently introduced to the second rectification column operating under conditions to reduce the concentration of the catalyst degradation product in the lights stream to produce the purified ester-substituted phenol product.

The method of the present invention has the benefit over other processes in that unreacted catalyst and other heavy components (such as unreacted dihydroxy monomers) are removed from the recycle stream in a first separation stage. This reduces and even can eliminate the possibility of generating additional catalyst degradation product and other byproducts (e.g. dihydroxy monomer degradation products such as phenol) in later stages of separation. The present invention's methods are preferred over a process where catalyst degradation product and other light byproducts and light impurities are removed from the recycle stream in a first step leaving the removal of residual melt transesterification catalyst and other heavy components from the recycle stream for a subsequent step where additional catalyst degradation product and other light impurities and byproducts may be generated.

The present invention may be understood more readily by reference to the following detailed description of preferred embodiments of the invention and the examples included therein. In the specification and the claims which follow, reference will be made to a number of terms which shall be defined to have the following meanings:

The singular forms "a", "an", and "the" include plural referents unless the context clearly dictates otherwise.

"Polycarbonate" refers to polycarbonates incorporating repeat units derived from at least one dihydroxy aromatic compound and includes copolyestercarbonates, for example a polycarbonate comprising repeat units derived from resorcinol, bisphenol A, and dodecanedioic acid. Nothing in the description and claims of this application should be taken as limiting the polycarbonate to only one dihydroxy residue unless the context is expressly limiting. Thus, the application encompasses copolycarbonates with residues of 2, 3, 4, or more types of dihydroxy compounds.

"Recycle Stream" and "byproduct stream" are herein used to describe a stream of byproducts coming from a melt transesterification reaction to form polycarbonate. The recycle stream will have reaction byproducts of ester-substituted phenol and catalyst degradation product. The recycle stream will also have unreacted residual components from the melt transesterification reaction including residual ester-substituted diaryl carbonate and residual melt transesterification catalyst. In one embodiment, the recycle stream will further comprise unreacted and residual dihydroxy compounds, or monomers, from the melt transesterification reaction.

"Catalyst degradation product" refers to the trialkyl (amine or phosphine) that may be produced from a reaction in which a tetraalkyl (ammonium or phosphonium) hydroxide is used as a catalyst. The tetraalkyl (ammonium or phosphonium) hydroxide used as a catalyst has a methyl group for at least one of its alkyl groups. The resulting trialkyl (amine or phosphine) catalyst degradation product may also have a methyl group for at least one of its alkyl groups.

Numerical values in the specification and claims of this application reflect average values. Furthermore, the numerical values should be understood to include numerical values which are the same when reduced to the same number of significant figures and numerical values which differ from the stated value by less than the experimental error of the measurement technique used in the present application to determine the value.

US patent application publication no. 2006/0025622, which is incorporated herein by reference, discusses several techniques used to produce ester-substituted diaryl carbonates from ester-substituted phenols. As disclosed in that publication and above a preferred method of producing ester-substituted diaryl carbonates from ester-substituted phenols comprises the step of contacting ester-substituted phenol with phosgene in the presence of a tertiary amine catalyst, a phase transfer catalyst, or both. These catalysts have been found to accelerate the formation of ester-substituted diaryl carbonate product and to act to minimize the presence of the intermediate ester-substituted phenyl chloroformate in the product. Suitable phase transfer catalysts are widely available and include quaternary ammonium salts of aliphatic amines, quaternary ammonium salts of aromatic amines, quaternary phosphonium salts, sulfonium salts, polyethers and the like. The amount of phase transfer catalyst employed is typically in a range between 0.1 and 2 mole percent catalyst, and preferably between 0.25 and 1.0 mole percent catalyst per mole of ester-substituted phenol employed. In another embodiment of the present invention a tertiary amine is included as a catalyst for the formation of ester-substituted diaryl carbonates. The preferred tertiary amine used as a catalyst of the present invention is triethyl amine. The amount of the tertiary amine catalyst employed is typically in a range of between 0.01 and 1.00, for example between 0.01 and 0.09, mole percent catalyst based upon the number of moles of ester-substituted phenol employed in the reaction mixture.

Preferred processes for the formation of polycarbonate, or polycarbonate oligomers, using ester-substituted diaryl carbonates as a carbonate source are disclosed in US patent application publication nos. 2005/0234211 and 2006/0069228 which are both incorporated by reference. In these disclosures it is explained that non-ester substituted diaryl carbonates, such as DPC, may be replaced with ester-substituted diaryl carbonates, such as BMSC, to increase polymerization reaction rates. Further, in these disclosures it is explained that it is often preferred that the reaction of the ester-substituted diaryl carbonate with a dihydroxy composition be catalyzed by a catalyst such as quaternary ammonium or quaternary phosphonium hydroxides. Such hydroxides serve to promote the transesterification reaction between the carbonate source and the free hydroxyl ends of the dihydroxy compositions. For thermal stability, cost, and commercial availability reasons, inter alia, preferred examples of such compounds are tetramethyl ammonium hydroxide and tetramethyl phosphonium hydroxide. As the melt transesterification reaction proceeds the reaction components are consumed and the free-hydroxy ends of the dihydroxy monomers are linked to form polycarbonate. Upon the consumption of the ester-substituted diaryl carbonate a byproduct ester-substituted phenol is produced. Furthermore, upon the consumption of the catalysts, a catalyst degradation byproduct comprising a trialkyl amine (e.g. trimethyl amine), a trialkyl phosphine (e.g. trimethyl phosphine), or both are produced. Lastly, upon the consumption of dihydroxy monomer compositions a reaction byproduct including a non-ester substituted phenolic compound may be produced such as phenol or resorcinol, inter alia. These byproducts are removed as a crude ester-substituted phenol stream that is subjected to the methods of the present invention to produce a purified ester-substituted product stream.

Methods of Producing a Purified Ester-Substituted Phenol Stream:

The methods of the present invention remove unreacted residual melt transesterification catalyst and other heavy components such as residual unreacted dihydroxy monomers from the recycle stream prior to removing light components such as the catalyst degradation product. This ensures that additional catalyst degradation product and other light byproducts from the melt reaction are not generated during later stages of purifying the recycle stream.

In a first embodiment, the present invention provides a method of producing a purified ester-substituted phenol stream from a melt transesterification reaction byproduct stream, the method comprising the sequential steps of:
(a) obtaining from a melt transesterification reaction a byproduct stream comprising a residual ester-substituted diaryl carbonate, an ester-substituted phenol, a residual melt transesterification catalyst, and a catalyst degradation product,
wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and
wherein the catalyst degradation product comprises a trialkyl phosphine, a trialkyl amine, or both,
(b) treating the byproduct stream to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and
(c) treating the light recycle stream to reduce catalyst degradation product concentration, thereby producing a purified ester-substituted phenol stream.

The step of obtaining a byproduct stream from a melt transesterification reaction is accomplished by removing reaction byproducts from a melt polymerization reaction to form polycarbonate. As indicated above, in melt transesterification reactions to form polycarbonate, a reaction mixture is typically prepared that contains an ester-substituted diaryl carbonate, a dihydroxy monomer compound, and a melt transesterification catalyst. This reaction mixture is introduced to a melt polymerization reactor system operating under melt polymerization conditions. As the melt reaction proceeds to link the free hydroxy ends of the dihydroxy compounds the ester-substituted diaryl carbonate is consumed and a byproduct ester-substituted phenol is produced. To drive the reaction toward completion this ester-substituted phenol is removed, typically under vacuum as a vapor, from the melt polymerization reaction system. It has been found that, together with the ester-substituted phenol byproduct that melt transesterification catalyst degradation product and dihydroxy monomer byproduct such as a non-ester substituted phenolic compound may also be removed. Further the recycle stream may also comprise any or all of the following unreacted residual reactants including residual ester-substituted diaryl carbonate, residual dihydroxy monomer compounds, and residual melt transesterification catalysts.

The first treatment step to produce a light recycle stream and a heavy recycle stream is not particularly limited other than the light recycle stream comprises ester-substituted phenol and catalyst degradation product and the heavy recycle stream comprises residual ester-substituted diaryl carbonate and residual melt transesterification catalyst. In a preferred embodiment the light recycle stream will comprise less than 5.00 ppm of residual catalyst, more preferably less than 1.00 ppm of residual catalyst, and most preferably less than 0.10 ppm of residual catalyst.

The first treatment step may be accomplished by known separation methods. At a residual catalyst level above 1.00 ppm in the light recycle stream, the 2nd distillation step would likely require either a short residence time and low temperature (e.g. less than 125° C.) which means low pressure (e.g. less than 50 mbar) to separate the ester-substituted phenol before residual catalyst (e.g. TMAH) degrades, or a long residence time and high temperature (e.g. greater than 140° C.), until the TMAH is degraded and TMA has the time to evaporate and be isolated from the ester-substituted phenol. This last option is similar to a combination of a degradation reaction and a devolatilization operation.

The maximum acceptable residual catalyst concentration in the lights stream is equipment specific. In some cases a residual catalyst (TMAH) concentration greater than 1.00 ppm in the lights stream of the first treatment step could generate later reactivity issues. The most preferred residual catalyst concentration when TMAH is the catalyst is less than 1.00 ppm and more preferably less than 0.10 in the lights of the first treatment step. The more preferred level would ensure minimal TMA production in the later refinement steps and in the final product even if all TMAH is later degraded.

In another embodiment the ester-substituted phenol recycle stream will further comprise a residual dihydroxy monomer compound and/or dihydroxy monomer degradation product (e.g. a non-ester-substituted phenolic compound such as phenol). In this embodiment the first treatment step will produce a light recycle stream further comprising dihydroxy monomer degradation product, if present in the byproduct stream, while the heavy recycle stream will further comprise residual dihydroxy monomer compound. In a preferred embodiment the lights recycle stream will comprise less than 200 ppm and more preferably less than 100 ppm dihydroxy monomer compound. Separating the residual dihydroxy monomer compound from the recycle stream in the first treatment step ensures that dihydroxy monomer degradation product is not significantly produced during later refinement steps in the purification process.

The second treatment step of treating the light recycle stream to reduce catalyst degradation product concentration is likewise not particularly limited. In a preferred embodiment the treatment step occurs such that less than 1.00 ppm, more preferably less than 0.75 ppm, for example less than 0.50 ppm, less than 0.25 ppm, and most preferably less than 0.10 ppm of catalyst degradation product is present in the product purified ester-substituted phenol stream.

In the embodiment described above where the ester-substituted phenol recycle stream further comprises residual dihydroxy monomer compound and/or dihydroxy monomer degradation product, the second treatment step will occur such that less than 200 ppm, more preferably less than 100 ppm, and most preferably less than 50 ppm of the dihydroxy monomer degradation product is present in the purified ester-substituted phenol product stream.

The dihydroxy monomer compound used to produce polycarbonate is not particularly limited. See above. The dihydroxy monomer degradation product is dependent upon the dihydroxy monomer used in the production of polycarbonate. In one embodiment of the present invention, the dihydroxy monomer compound comprises a bisphenol and the dihydroxy monomer degradation product comprises a non-ester substituted phenolic compound. Non-limiting examples of the non-ester substituted phenolic compound include aromatics such as phenol and others. In this embodiment the second treatment step occurs such that less than 100 ppm of the non-ester substituted phenolic compound is present in the recycled product ester-substituted phenol stream.

The reaction to form ester-substituted diaryl carbonate generally will require higher excess phosgene when TMA is higher than 0.10 ppm. As detailed in U.S. patent application Ser. No. 11/421,359 filed on May 31, 2006, discussed above, without excess phosgene more than 3% conversion loss was observed when using ester substituted phenol with 0.25 ppm TMA. In the present case and for the sake of process efficiency catalyst degradation product (e.g. TMA) concentration in the final product stream is preferably less than 0.20 ppm and most preferably less than 0.10 ppm.

Since trialkyl amines and phosphines are soluble in water, it has been found that the light recycle stream can be washed with water in a water extractor system to reduce the concentration of the catalyst degradation product. It has also been found that acid-scrubbing of the light recycle ester-substituted phenol stream is a suitable method of extracting the catalyst degradation product. In a further embodiment, the concentration of the catalyst degradation product may be reduced by diluting the light recycle stream with a stream of ester-substituted phenol containing less catalyst degradation product than the light recycle stream, for example a stream of pure ester-substituted phenol.

It has however herein been found to be preferred that the first and second treatment steps occur via the use of at least two rectification columns. In this preferred embodiment the present invention provides a method of producing a purified ester-substituted phenol stream from a melt transesterification reaction byproduct stream, the method comprising the sequential steps of:

(a) obtaining from a melt transesterification reaction a byproduct stream comprising a residual ester-substituted diaryl carbonate, an ester-substituted phenol, a residual melt transesterification catalyst, and a catalyst degradation product, wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and wherein the catalyst degradation product comprises a trialkyl phosphine, a trialkyl amine, or both, (b) introducing the byproduct stream to a first rectification column operating under conditions to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and (c) introducing the light recycle stream to a second rectification column operating under conditions to separate catalyst degradation product from ester-substituted phenol, thereby creating a catalyst degradation product stream and a purified ester-substituted phenol stream, wherein the ester-substituted phenol stream has less than 1.00 ppm catalyst degradation product present.

The first rectification tower is operated under conditions sufficient to separate ester-substituted phenol and catalyst degradation product from residual ester-substituted diaryl carbonate and residual melt transesterification catalyst. In this first rectification column a top lights recycle stream is produced comprising ester-substituted phenol and catalyst degradation product.

Further, a heavy bottom product is produced comprising residual ester-substituted diaryl carbonate and residual melt transesterification catalyst.

Depending on, inter alia, the number of column stages (i.e. separation trays), the feed entry stage, material flow rates, the operating pressures and temperatures of the column, and the initial makeup of the byproduct stream, the compositions of the top light recycle stream and bottom heavy recycle stream will vary. Thus in some embodiments the top lights recycle stream will further comprise residual melt transesterification catalyst. In this embodiment, it is preferred that the first rectification column be operated under conditions sufficient to produce a top lights recycle stream comprising less than 5.00 ppm of residual catalyst, more preferably less than 1.00 ppm residual catalyst, and most preferably less than 0.10 ppm residual catalyst.

The second rectification column is operated under conditions sufficient to separate catalyst degradation product from ester-substituted phenol. In this second rectification column a catalyst degradation product stream is produced and claimed in a top light product and a purified ester-substituted phenol stream is produced and claimed as a bottom heavy product. As with the first rectification column the purified ester-substituted phenol stream claimed from the bottom of the column may further comprise a trace amount of catalyst degradation product depending on, inter alia, the number of column trays, the feed entry stage, material flow rates, the operating pressures and temperatures of the column, and the initial makeup of the lights recycle stream coming from the first column. In this instance, it is preferred that second rectification column be operated under conditions sufficient to produce a purified ester-substituted phenol stream comprising less than 1.00 ppm, more preferably less than 0.75 ppm, for example less than 0.50 ppm, less than 0.25 ppm, and most preferably less than 0.10 ppm of catalyst degradation product is present in the product purified ester-substituted phenol stream.

Where the byproducts stream further comprises residual dihydroxy monomer compound and/or dihydroxy monomer degradation product, step (b) is performed to create a light recycle stream further comprising dihydroxy monomer degradation product and a heavy recycle stream further comprising residual dihydroxy monomer compound, and step (c) is performed to produce a catalyst degradation product stream further comprising dihydroxy monomer degradation product and a purified ester-substituted phenol stream, wherein the ester-substituted phenol stream has less than 1.00 ppm catalyst degradation product present and less than 200 ppm, more preferably less than 100 ppm, dihydroxy monomer degradation product present.

In a further embodiment the methods of the present invention may further comprise a third treatment step of introducing the purified ester-substituted phenol stream to a single-stage separator. In this embodiment, the purified ester-substituted stream may be further treated to remove remaining catalyst degradation product and/or color bodies that may be present to further purify the product stream. Single-stage separators are not particularly limited and include, for non-limiting example, a wiped film evaporator, a flash tank, or an internal condenser that is coupled to a side-draw product stream that is disposed within the second rectification column above the boiler.

In a preferred embodiment the treatment steps also serve to remove color bodies and/or products that are capable of generating color. Non-limiting examples of compounds capable of generating color and color bodies include, hydroquinone, methyl hydroquinone, resorcinol, p-benzoquinine, methyl benzoquinone as well as a number of unknowns which are a result of a reaction or degradation of one or more of the byproducts present.

In this preferred embodiment the first and second treatment steps or the first, second, and third treatment steps are performed to produce an ester-substituted phenol stream having an APHA color less than 50 Hazen, preferably less than 25 Hazen, and more preferably less than 15 Hazen.

Uses of the Purified Ester-substituted Phenol and a Method of Producing a Purified Ester-substituted Diayl Carbonate:

The uses for the purified ester-substituted phenol stream produced by the methods of the present invention are not particularly limited. In a preferred embodiment the purified ester-substituted phenol stream will be used as a precursor in the preparation of ester-substituted diaryl carbonate.

The method of producing the ester-substituted diaryl carbonate from the purified ester-substituted phenol stream is likewise not particularly limited and can be accomplished via known methods, for example those described above. In a typical method the ester-substituted phenol will be contacted with phosgene, preferably in the presence of a catalyst such as triethyl amine, to produce the ester-substituted diaryl carbonate. Thus, in a further embodiment the present invention provides a method of producing an ester-substituted diaryl carbonate from a purified ester-substituted phenol stream from a melt transesterification reaction byproduct stream, the method comprising the sequential steps of:

(a) obtaining from a melt transesterification reaction a byproduct stream comprising a residual ester-substituted diaryl carbonate, an ester-substituted phenol, a residual melt transesterification catalyst, and a catalyst degradation product, wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and wherein the catalyst degradation product comprises a trialkyl phosphine, a trialkyl amine, or both, (b) introducing the byproduct stream to a first rectification column operating under conditions to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and (c) introducing the light recycle stream to a second rectification column operating under conditions to separate catalyst degradation product from ester-substituted phenol, thereby creating a catalyst degradation product stream and a purified ester-substituted phenol stream, wherein the ester-substituted phenol stream has less than 1.00 ppm catalyst degradation product present, (d) contacting the ester-substituted phenol stream with phosgene under conditions sufficient to form ester-substituted diaryl carbonate, thereby forming ester-substituted diaryl carbonate.

The uses for the ester-substituted diaryl carbonate produced by the methods of the present invention are not particularly limited. In a preferred embodiment the ester-substituted diaryl carbonate will be used as a carbonate source in the melt production of polycarbonate as disclosed in the references cited above. For example, the present invention provides an improved method of making polycarbonate using a carbonate source comprising an ester-substituted diaryl carbonate prepared by reacting phosgene with a purified ester-substituted phenol stream from the above methods.

The Ester-substituted Diaryl Carbonate:

In one aspect of the present invention a method is provided for the preparation of ester-substituted diaryl carbonates having structure I from a recycle stream of ester-substituted phenols having structure II,

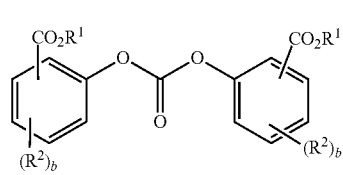

I wherein $R^1$ is independently at each occurrence a $C_1$-$C_{20}$ alkyl radical, $C_4$-$C_{20}$ cycloalkyl radical, or $C_4$-$C_{20}$ aromatic radical; $R^2$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and b is independently at each occurrence an integer from 0-4.

Examples of ester-substituted diaryl carbonates which may be prepared using the method of the present invention include bis-methyl salicyl carbonate (i.e. BMSC) (CAS Registry No. 82091-12-1), bis-ethyl salicyl carbonate, bis-propyl salicyl carbonate, bis-butyl salicyl carbonate, bis-benzyl salicyl carbonate, bis-methyl 4-chlorosalicyl carbonate and the like. Typically bis-methyl salicyl carbonate is preferred for use in melt polycarbonate synthesis due to its lower molecular weight and higher vapor pressure.

The Ester-substituted Phenol:

The recycle stream of ester-substituted phenol used in accordance with the present invention comprises at least one compound selected from among phenols having structure II,

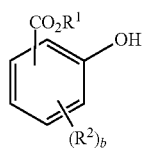

II wherein $R^1$, $R^2$, and b are defined as in structure I.

Examples of ester-substituted phenols which may serve as starting materials for the method of the present invention include phenyl salicylate, methyl salicylate (i.e. MS), ethyl salicylate, propyl salicylate, butyl salicylate, benzyl salicylate, methyl 4-chloro salicylate and the like. Typically, MS is a byproduct of transesterification reactions using BMSC. Further, MS is the preferred ester-substituted phenol used in the preparation of BMSC as described in the patents cited above. Further, recycled MS may be used to form BMSC according to the present invention.

Reaction Catalysts and Their Degradation Products:

As detailed above preferred polymerization catalysts used in the melt production of polycarbonate include tetraalkyl ammonium hydroxides and tetraalkyl phosphonium hydroxides having structure III,

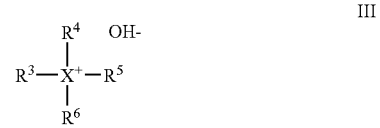

III wherein $R^3R^6$ represent alkyl groups having from 1 to 30, for example 1 to 4, carbon atoms in length; at least one of the $R^3$-$R^6$ groups is a —($CH_3$) group; and X+ represents phosphorus or nitrogen.

Suitable and non-limiting examples of tetraalkyl ammonium hydroxides and tetraalkyl phosphonium hydroxides having structure III are tetramethyl phosphonium hydroxide, diethyldimethyl phosphonium hydroxide, tetramethyl ammonium hydroxide, and diethyldimethyl ammonium hydroxide.

As a reaction proceeds, using a catalyst of structure III, a catalyst degradation product may be formed. The catalyst degradation product, depending on the selected catalyst will have structure IV,

IV wherein $R^7$-$R^9$ represent alkyl groups having from 1 to 30, for example 1 to 4, carbon atoms in length; and X− represents phosphorus or nitrogen. When the catalyst having structure III has one —($CH_3$) group, one of the $R^7$-$R^9$ groups may be a —($CH_3$) group. When the catalyst having structure III has at least two —($CH_3$) groups, at least one of the $R^7$-$R^9$ groups will be a —($CH_3$) group. For example when the catalyst having structure III is tetramethyl ammonium hydroxide (TMAH), the catalyst degradation product, if present, comprises trimethyl amine (TMA). If the catalyst having structure IV is tetramethyl phosphonium hydroxide, the catalyst degradation product, if present, comprises trimethyl phosphine. If both a tetramethyl(phosphonium and ammonium)hydroxide are used as catalysts, both a trimethyl(phosphine and amine) may be present in the catalyst degradation product.

In another embodiment where the catalyst having structure III is diethyldimethyl phosphonium hydroxide, the catalyst degradation product, if present, comprises diethylmethyl phosphine, ethyldimethyl phosphine, or a combination thereof. In yet a further embodiment where the catalyst having structure III is a diethyldimethyl ammonium hydroxide, the catalyst degradation product, if present, comprises diethylmethyl amine, ethyldimethyl amine, or a combination thereof.

EXAMPLES

Having described the invention in detail, the following examples are provided. The examples should not be considered as limiting the scope of the invention, but merely as illustrative and representative thereof.

Color was measured via AHPA standards. APHA is a traditional color measurement scale adapted by American Pharma Health Association. Normal ASTM methods also give this measurement, with the standard Pt.Cobalt scale 0-500. According to a proposal by A. Hazen in 1892, the Pt—Co/Apha-/Hazen color scale uses an acidic solution of potassium hexachloro-platinate(IV) and cobalt(II) chloride. The reference solutions are designated according to their platinum content in mg/L in the range 0-500. The solutions can be obtained from commercial suppliers.

Example 1—Comparative Example (Continuous Distillation—Lights Removal Followed by Heavies Removal)

The process commonly used for the purification of a mixture comprising numerous light and heavy components is to proceed with lights removal followed by heavies removal, where the final product will be evaporated and then condensed in the top of the heavies removal column to avoid contamination of the final product for example by metals or entrainment of traces of heavies. A process scheme for this example can be found in FIG. 1. Typical crude ester-substituted phenol specifications and desired purified ester-substituted phenol specification can be found in Table 2.

Step 1: Lights Removal

Figure 2:
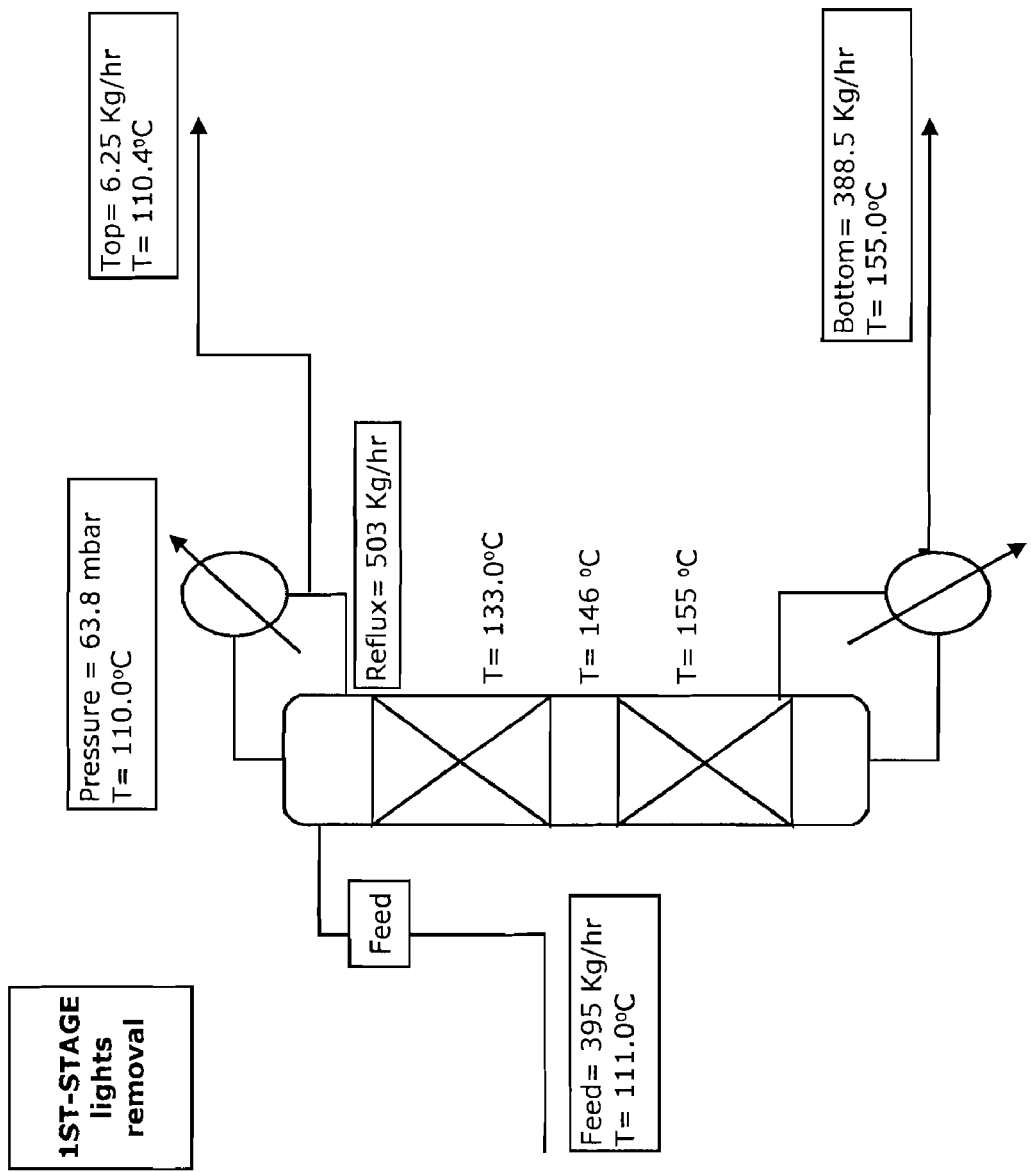

Crude MS is preheated to 111° C. in order to improve separation in the distillation column. The liquid stream is then fed to the first distillation column (=400 mm/11 NTS (NTS=number of theoretical stages) including condenser and re-boiler) above the second NTS. A fraction of the methyl salicylate (MS) mixture rich in lights is then evaporated under low pressure (64 mbar) before being condensed. The reflux to distillate ratio is 80, and 98.4% of the feed is collected from the bottom of the first distillation column. The top stream has a yellow color and is rich in lights, especially phenol and TMA. The bottom, however, is richer in MS, and heavies especially Ethyl Salicylate (ETS), Benzoic acid 2-Methoxymethyl Ester (MOB) and has only traces of TMA (<10 ppb). Phenol concentration in the bottom product is below the desired upper limit of 100 ppm (Table 1). The process conditions for this distillation column can be found in FIG. 2. The feed color is brownish with a measured APHA color greater than 305 Hazen. The condensed distillate product is yellow while the bottom product is still slightly colored ranging between 69 and 140 Hazen.

TABLE 1

MS lights removal step composition and mass balance.

|  | # | Feed Avg | Kg/hr | Distillate Avg | Kg/hr | Residue 1 Avg | Kg/hr | % Mass balance |
|---|---|---|---|---|---|---|---|---|
| Methyl-salicylate (MS) | (%) | 99.5 | 392.6 | 94.6 | 5.9 | 99.6 | 387.0 | 100 |
| Trimethyl amine (TMA) | (ppm) | 0.3 | 1E−04 | 36.0 | 2E−04 | 0.0 | 0E+00 | 204 |
| Tetra Methyl Ammonium Hydroxide (TMAH) | (ppm) | 2.6 | 1E−03 | 0.0 | 0E+00 | 2.6 | 1E−03 | 102 |
| Tot Unknowns | (ppm) | 1165 | 0.5 | 2128 | 0.0 | 1272 | 0.5 | 110 |
| Phenol (PhOH) | (ppm) | 1596 | 0.6 | 84134 | 0.5 | 68 | 0.0 | 88 |
| Hydroquinone (HQ) | (ppm) | 19 | 0.0 | 232 | 0.0 | 12 | 0.0 | 83 |
| EthylSalicylate (ETS) | (ppm) | 61 | 0.0 | 20 | 0.0 | 58 | 0.0 | 94 |
| Resorcinol (RS) | (ppm) | 0 | 0.0 | 0 | 0.0 | 0 | 0.0 |  |
| Benzoic acid, 2-methoxymethylester (MOB) | (ppm) | 326 | 0.1 | 52 | 0.0 | 353 | 0.1 | 107 |
| Methylhydroquinone (MeHQ) | (ppm) | 0 | 0.0 | 0 | 0.0 | 0 | 0.0 |  |
| Di-phenyl Carbonate (DPC) | (ppm) | 2054 | 0.8 | 279 | 0.0 | 2061 | 0.8 | 99 |
| Diethyl-Carbamate of MS | (ppm) | 2 | 0.0 | 2 | 0.0 | 2 | 0.0 | 96 |
| Para-cumyl Phenol (PCP) | (ppm) | 15 | 0.0 | 16 | 0.0 | 15 | 0.0 | 102 |

TABLE 2

Crude feed versus desired product specifications.

| Crude MS Component | UOM | Min | Max | Recycled MS specs Low spec | Recycled MS specs High Spec | Structure | Mw |
|---|---|---|---|---|---|---|---|
| MS(=Benzoic acid, 2-hydroxy-methylester) | wt % | 96.4 | 99.8 | 99.9 |  | 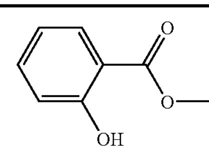 | 152 |
| Color | APHA | 200 | >700 | 25 |  |  |  |
| TMA (Tri-methyl amine) | ppm | 0.2 | 0.5 | 0.1 |  | 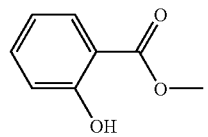 | 59 |

TABLE 2-continued
Crude feed versus desired product specifications.
| Crude MS Component | UOM | Min | Max | Recycled MS specs Low spec | Recycled MS specs High Spec | Structure | Mw |
|---|---|---|---|---|---|---|---|
| PhOH | ppm | 460 | 10400 |  | 100 | 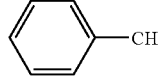 | 94 |
| MeBQ | ppm | 10 | 26 |  | 10 | 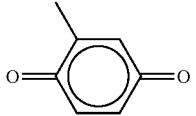 | 122 |
| HQ | ppm | 0 | 260 |  | 10 | 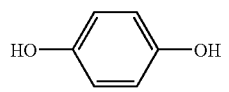 | 110 |
| RS | ppm | 0 | 6 |  | 10 | 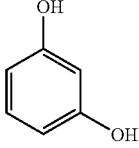 | 110 |
| MeHQ | ppm | 0 | 150 |  | 10 | 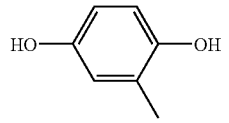 | 124 |
| PCP | ppm | 13 | 420 |  | 10 | 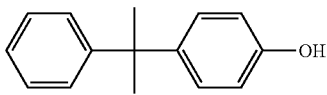 | 212 |
| BPA | ppm | 0 | 33000 |  | 10 | 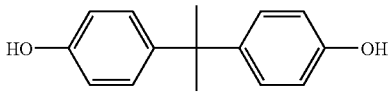 | 228 |
| BMSC | ppm | 6 | 136 |  | 10 | 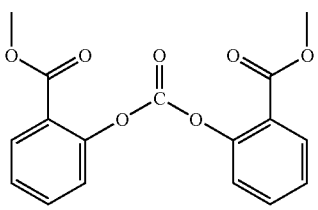 | 330 |
| Benzoic acid, 2-hydroxy-ethylester EthylSalycilate | ppm | 0 | 68 |  | 100 | 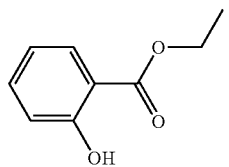 | 166 |

TABLE 2-continued

Crude feed versus desired product specifications.

| Crude MS Component | UOM | Min | Max | Recycled MS specs Low spec | Recycled MS specs High Spec | Structure | Mw |
|---|---|---|---|---|---|---|---|
| Benzoic acid, 2-hydroxy-, 3/4/5-methyl, methylester MS Methyl, 3/4/5 | ppm | 0 | 100 | | 100 | 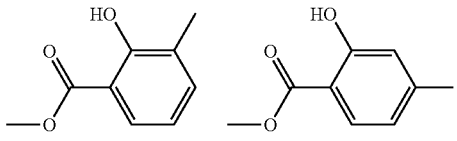 | 166 |
| Benzoic acid, 2-methoxymethylester (MOB) | ppm | 7 | 445 | | 100 | 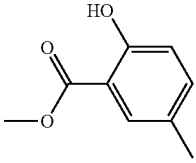 | 166 |
| MethylCarbonate of methylsalycilate MS MethylCarbonate | ppm | 0 | 100 | | 100 | 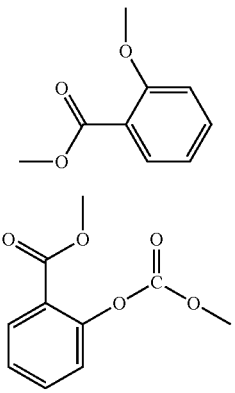 | 210 |
| 1,5-benzenedicarboxylic acid, 2-hydroxy-, dimethylester MS MethylSalycilate | ppm | 0 | 100 | | 100 | 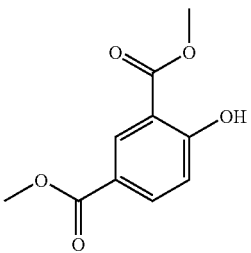 | 210 |
| Other impurities | ppm | 100 | 700 | | 300 | | |

Step 2: Heavies Removal

Figure 3:
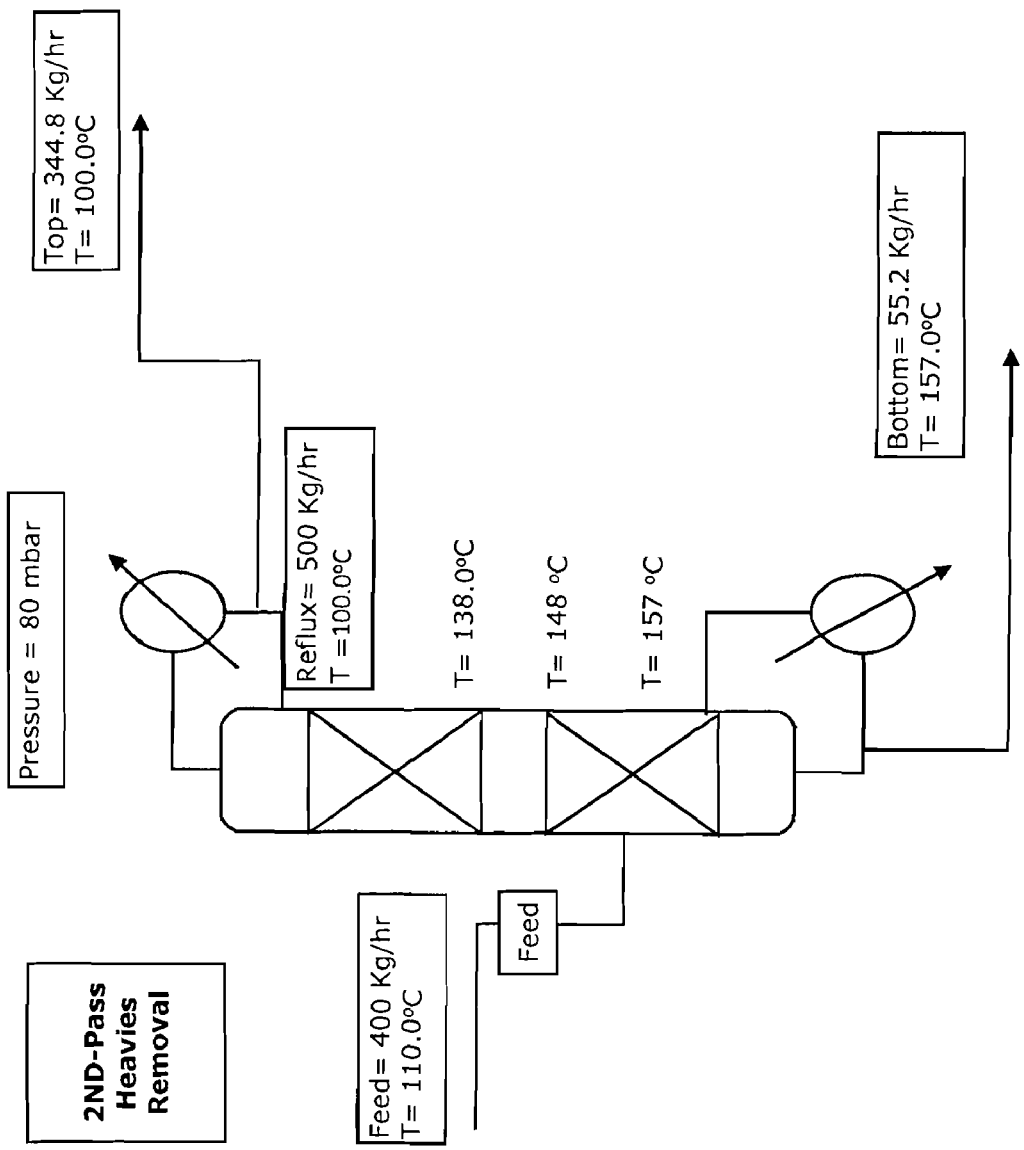

The bottom product from the first step is then preheated to 110° C. in order to improve separation in the second distillation column and fed above the reboiler of the second distillation column (=400 mm/11 NTS including condenser and re-boiler). Reflux over distillate ratio is 1.45 with low pressure in the top of the column (80 mbar). Further operating conditions can be found in FIG. 3.

A higher temperature in the bottom is observed compared to the first distillation column of the lights removal due to the lower boiling lights concentration in the feed to the second column. The mass balance is only approaching 100% for MS and ETS in this heavies removal step. The top distillation MS product has a purity of greater than 99.9%. Phenol increased by 4.5 times in the top product. 50% to 60% of the diphenyl carbonate (DPC), para cumyl phenol (PCP), hydroquinone (HQ) as well as unknown organics are in the bottoms product. Phenol concentration increased from 65 ppm in the feed to exceed the 335 ppm in the top condensate of the distillation column. The color of the top distillate MS is undesirable and is between 37 and 73, and on average 43 Hazen against an upper desired limit of 25 Hazen.

Figure 4:
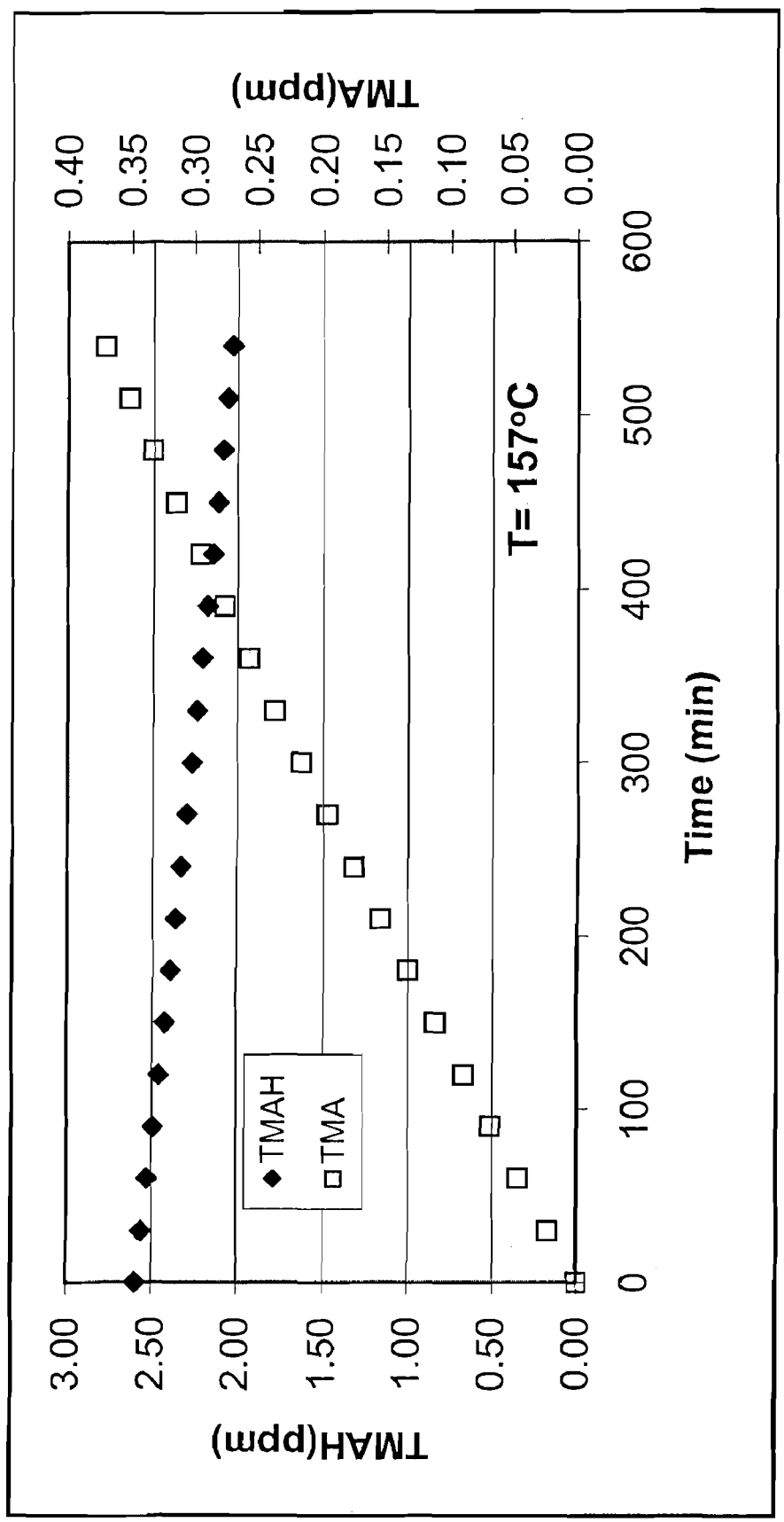
FIGS. 4 and 6 are graphical representations of results from the example section.

TMA in the feed of the heavies removal column is less than 0.01 ppm and under the desired limit. However, the distillate of the second distillation column is found to have 0.13 ppm of TMA, which is a significant increase and above the desired limit. Tetra-methyl ammonium hydroxide (TMAH) is a heavy and it was found that under high temperature TMAH degrades and produces TMA. FIG. 4 below shows the kinetic of degradation of TMAH to form TMA as function of time under 157° C.

TABLE 3

MS heavies removal step composition and mass balance.

| | | Feed Avg | Kg/hr | Distillate Avg | Kg/hr | Residue 1 Avg | Kg/hr | % Mass balance % |
|---|---|---|---|---|---|---|---|---|
| Methyl-salicylate (MS) | (%) | 99.6 | 398.5 | 99.9 | 344.6 | 98.9 | 54.6 | 100 |
| Trimethyl amine (TMA) | (ppm) | 0.0 | 0.0 | 0.13 | 0.0 | 0.0 | 0.0 | 564 |
| Tetra Methyl Ammonium Hydroxide (TMAH) | (ppm) | 2.6 | 0.0 | 0.0 | 0.0 | 6.0 | 0.0 | 33 |
| Tot Unknowns | (ppm) | 1242.6 | 0.5 | 130.9 | 0.0 | 3988.3 | 0.2 | 53 |
| Phenol (PhOH) | (ppm) | 65.6 | 0.0 | 335.0 | 0.1 | 57.9 | 0.0 | 452 |
| Hydroquinone (HQ) | (ppm) | 8.9 | 0.0 | 0.0 | 0.0 | 19.4 | 0.0 | 30 |
| EthylSalicylate (ETS) | (ppm) | 57.8 | 0.0 | 49.8 | 0.0 | 117.2 | 0.0 | 102 |
| Resorcinol (RS) | (ppm) | 0.0 | 0.0 | 0.0 | 0.0 | 0.0 | 0.0 | 0 |
| Benzoic acid, 2-methoxymethylester (MOB) | (ppm) | 336.9 | 0.1 | 1.1 | 0.0 | 1036.7 | 0.1 | 43 |
| Methylhydroquinone (MeHQ) | (ppm) | 0.0 | 0.0 | 0.0 | 0.0 | 0.0 | 0.0 | 0 |
| Di-phenyl Carbonate (DPC) | (ppm) | 2009.6 | 0.8 | 0.0 | 0.0 | 5843.7 | 0.3 | 40 |
| Para-cumyl Phenol (PCP) | (ppm) | 14.1 | 0.0 | 1.5 | 0.0 | 38.4 | 0.0 | 46 |

Conclusion:

The desired MS purity and desired color was not met by the combination of lights removal followed by heavies removal step. It was observed that the catalyst degradation product TMA and phenol largely increased in the distillate of the second distillation column exceeding the desired limits. It is believed that heavies like DPC, PCP, or HQ present in the feed mixture to the heavies removal step (second distillation column) degraded to produce this excess phenol. It is also believed that the residual TMAH catalyst degraded to produce the excess TMA.

TABLE 4

Comparative Example's summary

| | Feed | Lights removal | | Heavies Removal | |
|---|---|---|---|---|---|
| | | top | Bottom | top | Bottom |
| Purity % | 99.5 | 94.6 | 99.6 | 99.9 | 98.9 |
| Trimethyl amine (TMA) ppm | 0.3 | 36 | 0 | 0.13 | 0 |
| Phenol (ppm) | 1596 | 84134 | 68 | 335 | 58 |
| APHA (Hazen) | 305 | 140 | 69 | 43 | Red |

Example 2—Invention Example (Continuous Distillation—Heavies Removal/Lights Removal)

The present example reverses the order of removal from that illustrated in Example 1. In this example the distillation steps start with heavies removal first followed by lights removal. This allows the removal of heavy impurities (i.e. those with byproduct generating compounds first). These heavies are also a potential source of color. Once the heavies are removed, it is possible to remove lights and remaining color bodies without further impurities/byproduct generation in the second distillation column (lights removal column).

In the first step greater than 98.7% of the feed mixture is evaporated and condensed as a top product in a distillation column. The rest is withdrawn from the bottom of the column as heavies. The potential source of further generation of phenol, TMA, and color has therefore been eliminated.

Figure 5:
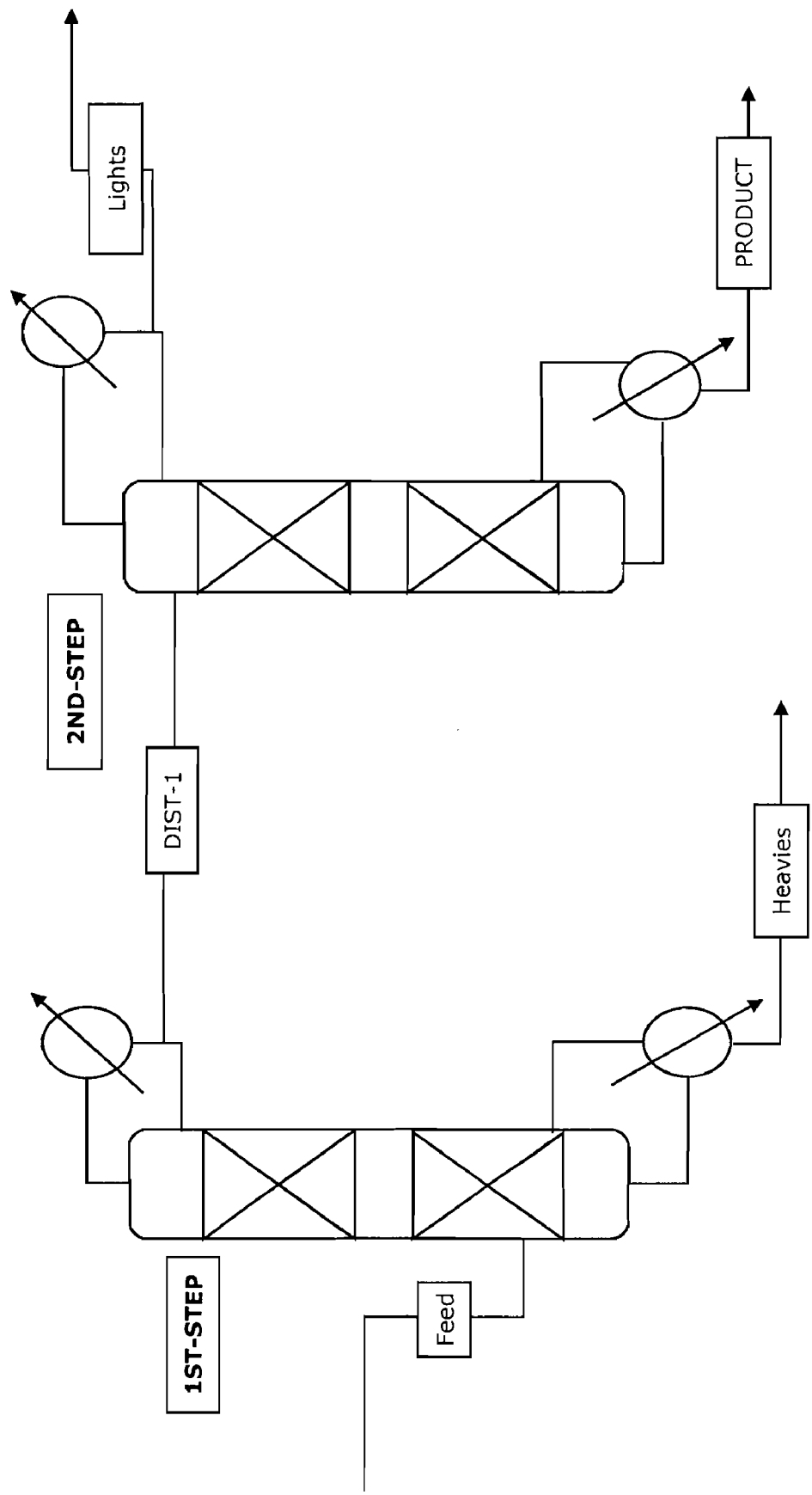

The separation scheme is depicted in FIG. 5. As shown, a crude MS mixture is fed to the bottom of the first distillation column preferably above theoretical stage=(n−1). Theoretical stage 1 is the condenser and theoretical stage n is the reboiler. The tops product of the first distillation column is fed to the second column for lights removal. The entry to the second distillation column is preferably below stage 2. The purified MS product is collected from the bottom of the second distillation column with a purity greater than 99.9% MS, less that 0.01 ppm TMA, and phenol below the detection limit. The APHA color was less than 25 Hazen.

Step 1. Heavies Removal

Table 5 is a mass balance around the first distillation column aimed to heavies removal. The feed mixture is fed to the bottom of the distillation column. 98.7% of the feed mixture is evaporated and condensed in the top of the column. The rest is withdrawn from the bottom of the distillation column. The feed mixture has an APHA color of greater than 700 Hazen. The top product has an APHA color of 58 while the bottom product is rich in heavies and has a red color. The top product is rich in lights especially phenol and TMA. The mass balance confirms degradation of TMAH in favor of TMA formation.

TABLE 5

MS heavies removal step composition and mass balance.

| Sample | | Date | feed | Kg/hr | top | Kg/hr | bottom | Kg/hr | % Mass balance |
|---|---|---|---|---|---|---|---|---|---|
| Reflux/Distillate | | | 0.75 | | 0.75 | | 0.75 | | |
| Bottom split | | | 0.012 | | 0.012 | | 0.012 | | |
| Methyl-salicylate (MS) | (%) | | 99.6 | 398.2 | 99.7 | 394.8 | 90.4 | 4.5 | 100 |
| Trimethyl amine (TMA) | (ppm) | | 1.2 | 0.0 | 5.0 | 0.0 | 0.0 | 0.0 | 405 |
| Tetra Methyl Ammonium Hydroxide (TMAH) | (ppm) | | 2.3 | 0.0 | 0.4 | 0.0 | 22.1 | 0.0 | 29.5 |
| Tot Unknowns | (ppm) | | 599.3 | 0.2 | 25.0 | 0.0 | 33620.3 | 0.2 | 74 |
| p-benzoquinone (BQ) | (ppm) | | 8.3 | 0.0 | 17.8 | 0.0 | 135.8 | 0.0 | 231 |
| Phenol (PhOH) | (ppm) | | 2677.5 | 1.1 | 2844.4 | 1.1 | 0.0 | 0.0 | 105 |
| Methyl-p-benzoquinone (MeBQ) | (ppm) | | 25.2 | 0.0 | 23.0 | 0.0 | 207.7 | 0.0 | 100 |
| Ethylphenylester of MS | (ppm) | | 4.6 | 0.0 | 2.4 | 0.0 | 149.2 | 0.0 | 92 |
| Hydroquinone (HQ) | (ppm) | | 156.5 | 0.1 | 0.0 | 0.0 | 6964.6 | 0.0 | 56 |
| EthylSalicylate (ETS) | (ppm) | | 1.8 | 0.0 | 0.0 | 0.0 | 80.2 | 0.0 | 57 |

TABLE 5-continued

MS heavies removal step composition and mass balance.

| Sample | | feed | Kg/hr | top | Kg/hr | bottom | Kg/hr | % Mass balance |
|---|---|---|---|---|---|---|---|---|
| Resorcinol (RS) | (ppm) | 0.0 | 0.0 | 0.0 | 0.0 | 0.0 | 0.0 | |
| Benzoic acid, 2-methoxymethylester (MOB) | (ppm) | 383.5 | 0.2 | 11.1 | 0.0 | 20612.5 | 0.1 | 70 |
| Methylhydroquinone (MeHQ) | (ppm) | 104.0 | 0.0 | 0.0 | 0.0 | 4990.0 | 0.0 | 60 |
| Di-phenyl Carbonate (DPC) | (ppm) | 4.7 | 0.0 | 0.0 | 0.0 | 64.7 | 0.0 | 17 |
| Diethyl-Carbamate of MS | (ppm) | 104.6 | 0.0 | 0.0 | 0.0 | 5921.4 | 0.0 | 71 |
| Para-cumyl Phenol (PCP) | (ppm) | 419.2 | 0.2 | 0.0 | 0.0 | 23625.5 | 0.1 | 70 |

It has been found that a reflux ratio ranging between 0.2 and 0.5 would be an optimal window to operate the heavies removal step. Furthermore, a feed point 2 stages above the reboiler allows lower boiling heavies in the distillate of heavies removal. The more theoretical stages the better during the heavies removal.

Step 2: Lights Removal

The top product of the heavies removal step is fed preferably below stage 2 to prevent entrainment. 98.7% of the feed is collected as a bottom product, and the rest is condensed and withdrawn as the lights fraction. The purity of MS in the bottom product exceeds 99.9%. Phenol concentration is below detection limit while TMA is less 0.01 ppm and below the desired limit. The color of the bottom product ranges between 5 and 25 Hazen, which is within desirable limits of the purified MS. The top product is yellow and has an APHA color ranging between 79 and 135 with an average around 105 Hazen. The top product is rich in phenol, TMA and other lights.

TABLE 6

MS lights removal step composition and mass balance.

| Sample | | feed | Kg/hr | top | Kg/hr | bottom | Kg/hr | % Mass balance |
|---|---|---|---|---|---|---|---|---|
| Reflux/Distillate | | 20.80 | | 20.80 | | 20.80 | | |
| Bottom split | | 0.027 | | 0.027 | | 0.027 | | |
| Methyl-salicylate (MS) | (%) | 99.71 | 372.90 | 96.63 | 14.49 | 99.99 | 363.97 | 101 |
| Trimethyl amine (TMA) | (ppm) | 2.8 | 0.0 | 56.9 | 0.0 | 0.0 | 0.0 | 54 |
| Tetra Methyl Ammonium Hydroxide (TMAH) | (ppm) | 0.38 | 0.00 | 0.91 | 0.00 | 0.81 | 0.00 | 212 |
| Tot Unknowns | (ppm) | 22.7 | 0.0 | 17.7 | 0.0 | 27.2 | 0.0 | 119 |
| p-benzoquinone (BQ) | (ppm) | 17.72 | 0.01 | 217.05 | 0.00 | 0.00 | 0.00 | 33 |
| Phenol (PhOH) | (ppm) | 2792 | 1.0 | 31693 | 0.3 | 0.00 | 0.00 | 30 |
| Methyl-p-benzoquinone (MeBQ) | (ppm) | 23.5 | 0.0 | 551.1 | 0.0 | 0.0 | 0.0 | 63 |
| Ethylphenylester of MS | (ppm) | 2.97 | 0.00 | 0.00 | 0.00 | 3.03 | 0.00 | 99 |
| Hydroquinone (HQ) | (ppm) | 0.00 | 0.00 | 15.42 | 0.00 | 0.00 | 0.00 | |
| EthylSalicylate (ETS) | (ppm) | 2.63 | 0.00 | 0.00 | 0.00 | 0.00 | 0.00 | 0 |
| Resorcinol (RS) | (ppm) | 0.00 | 0.00 | 0.00 | 0.00 | 0.00 | 0.00 | |
| Benzoic acid, 2-methoxymethylester (MOB) | (ppm) | 8.35 | 0.00 | 0.00 | 0.00 | 10.16 | 0.00 | 118 |
| Methylhydroquinone (MeHQ) | (ppm) | 0.00 | 0.00 | 0.00 | 0.00 | 0.00 | 0.00 | |
| Di-phenyl Carbonate (DPC) | (ppm) | 0.00 | 0.00 | 2.61 | 0.00 | 0.00 | 0.00 | |
| Diethyl-Carbamate of MS | (ppm) | 0.00 | 0.00 | 9.85 | 0.00 | 0.00 | 0.00 | |
| Para-cumyl Phenol (PCP) | (ppm) | 0.00 | 0.00 | 0.00 | 0.00 | 0.00 | 0.00 | |

The MS produced is within desired specifications and could be used to produce high quality BMSC for the process.

Figure 6:
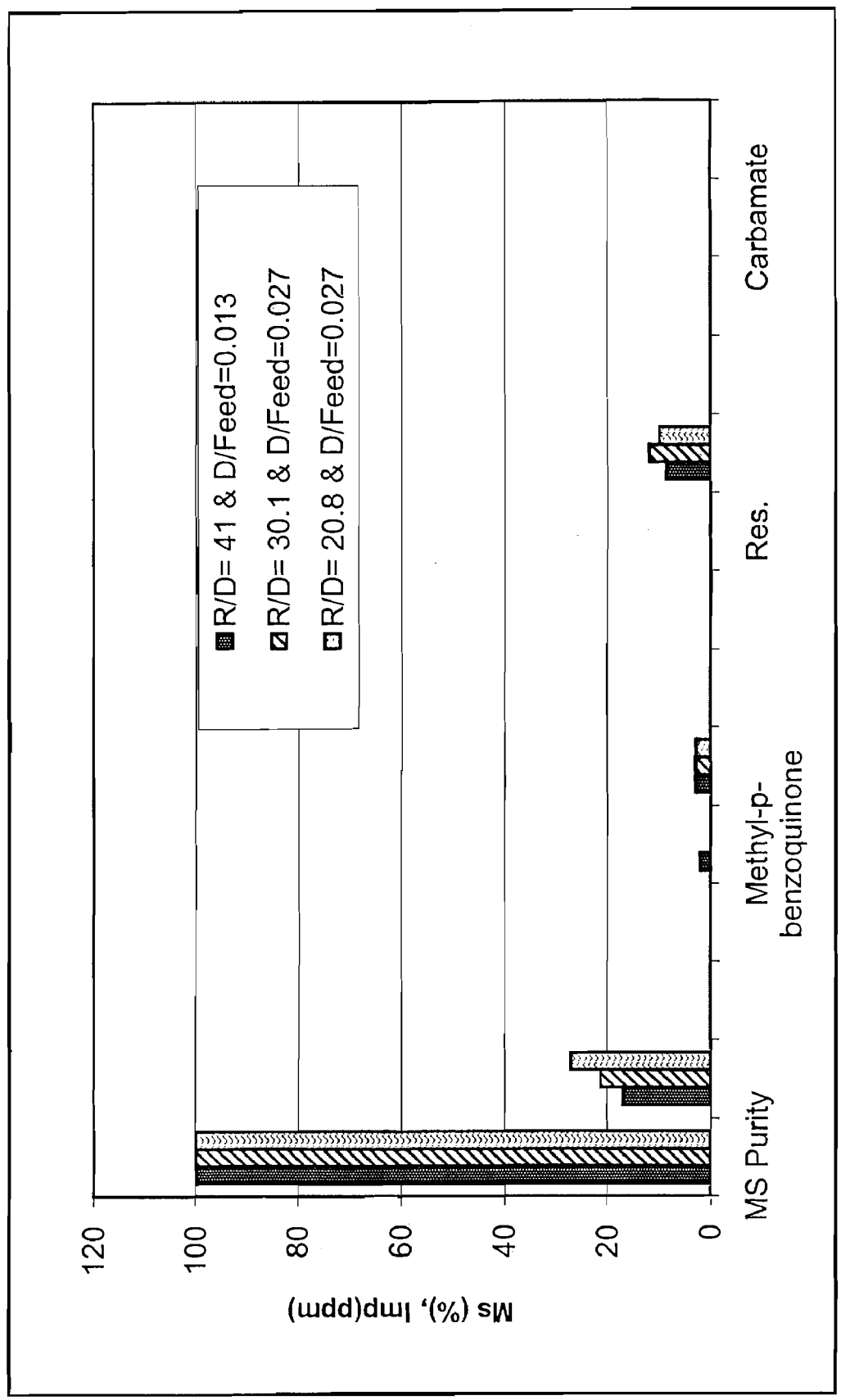

FIG. 6 below shows that there is an advantage in running a higher reflux ratio allowing lower heavies carryover. The optimal feed point is in the top section of the distillation column. Feeding above two stages after the reboiler has been proven sufficient for required MS purity and color.

Conclusion:

Desired MS purity and color are met by the combination of heavies removal followed by lights removal step. The feed to the heavies removal is better in the lower section of the column and typically 2 theoretical stages above the reboiler. The feed to the lights removal is better in the top section of the column and below the second theoretical stage (e.g., 2 stages below condenser). The reflux ratio reflux/distillate for the heavies removal ranges between 0.33 and 0.75, and is better at 0.33. For lights removal, it was found that the higher the reflux ratio the better the performance of the column. The reflux ratio ranges between 20 and 60 and preferably higher than 40.

TABLE 7

Example summary

| | Feed | Heavies Removal | | Lights removal | |
|---|---|---|---|---|---|
| | | top | Bottom | top | Bottom |
| Purity % | 99.5 | 99.7 | 90.4 | 96.6 | 99.99 |
| Trimethyl amine (TMA) ppm | 1.2 | 5 | 0 | 56.9 | 0 |

TABLE 7-continued

Example summary

| | Feed | Heavies Removal | | Lights removal | |
|---|---|---|---|---|---|
| | | top | Bottom | top | Bottom |
| Phenol (ppm) | 2792 | 2844.4 | 0 | 31693 | 0 |
| APHA (Hazen) | 700 | 58 | Red | 105 | 17.6 |

Example 3—Invention Example (A Polishing Distillation Step)

The product of the lights removal column of EXAMPLE 2 can be subject to heavies and color contamination. This is a reason why the design for the recycle stream purification would normally be to have lights removal followed by heavies removal as in EXAMPLE 1, where the final product will be collected overhead (from the second column) and avoid contamination with residuals from the column. However, with the reversed operating mode (e.g. EXAMPLE 2) a product having the desired MS purity can be produced. The material however, may still have undesired color properties. Using an additional theoretical stage, where the feed is the product from the bottom of the second distillation column and the final product is collected overhead, produces a product with in-spec color.

The bottom product of the lights removal column (from EXAMPLE 2) can be further treated to reduce color of the purified ester-substituted phenol stream in a subsequent purification step. Vaporizing the bottom material and condensing the vapor in an additional theoretical stage allows for the reduction of color and increased purity.

Table 8 below shows an example of a lights removal column producing a purified ester-substituted phenol with undesirable color. The material has an APHA color of 53 Hazen, while the purity is within desired limits. The use of a wiped film evaporator (WFE) allowed a distillate with an APHA of 10.3 Hazen

TABLE 8

Results of MS color polishing using a WFE.

| # | | Lights removal bottom | Lights removal bottom + WFE |
|---|---|---|---|
| Methyl-salicylate (MS) | (%) | 99.97 | 99.98 |
| Color | (APHA) | 53.0 | 10.3 |
| Tot Unknowns | (ppm) | 106.40 | 127.04 |
| Phenol (PhOH) | (ppm) | 1.55 | 4.92 |
| Hydroquinone (HQ) | (ppm) | 0.00 | 0.00 |
| EthylSalicylate (ETS) | (ppm) | 17.62 | 17.11 |
| Resorcinol (RS) | (ppm) | 0.00 | 0.00 |
| Benzoic acid, 2-methoxymethylester (MOB) | (ppm) | 65.00 | 56.36 |
| Methylhydroquinone (MeHQ) | (ppm) | 0.00 | 0.00 |
| Di-phenyl Carbonate (DPC) | (ppm) | 0.00 | 0.00 |
| Para-cumyl Phenol (PCP) | (ppm) | 3.40 | 0.46 |

The same result was obtained by using a batch flash unit or by applying an internal condenser in the lights removal column. This condenser is placed above the reboiler section, below the bottom packing bed.

TABLE 9

Results of MS color polishing using a batch flash unit.

| | Unit | lights removal bottom | Bottom product + 1 Theoretical stage |
|---|---|---|---|
| Color | (APHA) | 64.70 | 21.10 |
| Methyl-salicylate (MS) | (%) | 99.99 | 99.99 |
| Tot Unknowns | (ppm) | 61.73 | 57.73 |
| Tot Unknown lights | (ppm) | 30.96 | 24.23 |
| Total Unknown heavies | (ppm) | 30.76 | 33.50 |
| Phenol (PhOH) | (ppm) | 0.72 | 1.69 |
| Ethylphenylester of MS | (ppm) | 6.67 | 9.53 |
| Hydroquinone (HQ) | (ppm) | 0.00 | 0.00 |
| EthylSalicylate (ETS) | (ppm) | 3.36 | 4.56 |
| Resorcinol (RS) | (ppm) | 0.00 | 0.00 |
| Benzoic acid, 2-methoxymethylester (MOB) | (ppm) | 1.12 | 6.11 |
| Methylhydroquinone (MeHQ) | (ppm) | 0.00 | 0.00 |
| Di-phenyl Carbonate (DPC) | (ppm) | 0.00 | 0.00 |
| Diethyl-Carbamate of MS | (ppm) | 0.00 | 0.00 |
| Para-cumyl Phenol (PCP) | (ppm) | 0.00 | 0.00 |

The purpose of an internal condenser is to obtain the MS product after an evaporation step similar to the flash and the WFE. The condensate is collected in a hold up volume below the condenser and from there it flows to MS Recovery side draw purified MS collection tank. The bottom product below the condenser will be removed from the column sump and should be disposed. The condensed distillate of the heavies removal is fed to the heavies removal column now equipped with internal condenser in the bottom below the packing. The Reflux to distillate ratio is 30 and the yield was selected to be 95% of the feed mixture. The feed mixture is fed 2 theoretical stages below the condenser. Table 10 below shows that the side draw material from the internal condenser is of a high purity and has an APHA color of less than 5 Hazen.

TABLE 10 results of lights removal with internal condenser

| | | Lights Removal Feed | Side draw | Top collect | Bottom collect |
|---|---|---|---|---|---|
| Color | (APHA) | 41 | <5 | yellow | Red |
| Methyl-salicylate (MS) | (%) | 99.6 | 99.99 | 90.7 | 100.0 |
| Tot Unknowns | (ppm) | 86.1 | 48.27 | 955.1 | 198.0 |
| Tot Unknown lights | (ppm) | 66.6 | 20.11 | 516.6 | 30.6 |
| Total Unknown heavies | (ppm) | 19.5 | 28.16 | 438.5 | 167.4 |
| p-benzoquinone (BQ) | (ppm) | 9.9 | 0.00 | 200.0 | 2.6 |
| Phenol (PhOH) | (ppm) | 4307.6 | 0.00 | 92024.9 | 2.0 |
| Methyl-p-benzoquinone (MeBQ) | (ppm) | 25.8 | 0.41 | 480.6 | 7.4 |
| Ethylphenylester of MS | (ppm) | 7.6 | 8.26 | 0.0 | 12.7 |
| Hydroquinone (HQ) | (ppm) | 0.0 | 0.00 | 0.0 | 0.0 |
| EthylSalicylate (ETS) | (ppm) | 2.9 | 4.11 | 0.0 | 5.8 |
| Resorcinol (RS) | (ppm) | 0.0 | 0.00 | 0.0 | 0.0 |
| Benzoic acid, 2-methoxymethylester (MOB) | (ppm) | 0.0 | 2.70 | 0.0 | 16.2 |
| Methylhydroquinone (MeHQ) | (ppm) | 0.0 | 0.00 | 0.0 | 0.0 |

TABLE 10-continued results of lights removal with internal condenser

| | | Lights Removal Feed | Side draw | Top collect | Bottom collect |
|---|---|---|---|---|---|
| Di-phenyl Carbonate (DPC) | (ppm) | 0.0 | 0.00 | 0.0 | 0.0 |
| Diethyl-Carbamate of MS | (ppm) | 0.0 | 0.00 | 0.0 | 6.5 |
| Para-cumyl Phenol (PCP) | (ppm) | 0.0 | 0.00 | 0.0 | 9.6 |

Conclusion:

Table 11 below shows a comparative summary of the different examples and comparative examples where it is found that heavies removal followed by lights removal is optimal for the purification of crude MS recycled from the melt polymerization process.

Adding an additional theoretical stage provides a supplemental step to the purification process and prevents contamination of MS either due to material of construction of the column or due to occasional entrainment of heavy color bodies.

TABLE 11

Summary of Crude MS purification examples

| | Comp. Exp Heavies + Lights | Example 1 Lights + Heavies | Example 2 Lights + Heavies + 1 Stage |
|---|---|---|---|
| Purity % | 99.9 | 99.99 | 99.99 |
| Trimethyl amine (TMA) ppm | 0.13 | 0 | 0 |
| Phenol (ppm) | 335 | 0 | 0 |
| APHA (Hazen) | 43 | 17.6 | 7 |

The invention claimed is:

1. A method of producing a purified ester-substituted phenol stream from a melt transesterification reaction byproduct stream, the method comprising the sequential steps of:
   (a) obtaining from a melt transesterification reaction a byproduct stream comprising a residual ester-substituted diaryl carbonate, an ester-substituted phenol, a residual melt transesterification catalyst, and a catalyst degradation product,
      wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and
      wherein the catalyst degradation product comprises a trialkyl phosphine, a trialkyl amine, or both,
   (b) treating the byproduct stream to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and
   (c) treating the light recycle stream to reduce catalyst degradation product concentration,
   thereby producing a purified ester-substituted phenol stream.

2. The method of claim 1, wherein step (b) is accomplished using a first rectification tower.

3. The method of claim 2, wherein step (c) is accomplished using a second rectification tower.

4. The method of claim 2, wherein step (c) is accomplished by washing the light recycle stream with an aqueous solution.

5. The method of claim 2, wherein step (c) is accomplished by mixing the light recycle stream with an ester-substituted phenol stream containing a lower concentration of the catalyst degradation product than the light recycle stream.

6. The method of claim 1, wherein the light recycle stream further comprises residual melt transesterification catalyst in an amount of less than 0.10 ppm.

7. The method of claim 1, wherein the purified ester-substituted phenol stream comprises less than 0.10 ppm of catalyst degradation product.

8. The method of claim 1, wherein:
   the tetraalkyl phosphonium hydroxide comprises tetramethyl phosphonium hydroxide, diethyldimethyl phosphonium hydroxide, or both,
   the tetraalkyl ammonium hydroxide comprises tetramethyl ammonium hydroxide, diethyldimethyl ammonium hydroxide, or both, and
   the catalyst degradation product is trimethyl phosphine, diethylmethyl phosphine, dimethylethyl phosphine, trimethyl amine, diethylmethyl amine, dimethylethyl amine, or any combination thereof.

9. The method of claim 1, wherein the byproduct stream further comprises a residual dihydroxy monomer compound and a dihydroxy monomer degradation product, wherein step (b) is performed to create a light recycle stream further comprising dihydroxy monomer degradation product and a heavy recycle stream further comprising residual dihydroxy monomer compound, and wherein step (c) is performed to reduce catalyst degradation product concentration and dihydroxy monomer degradation product concentration in the light recycle stream.

10. The method of claim 9, wherein the purified ester-substituted phenol stream comprises less than 100 ppm dihydroxy monomer degradation product.

11. A method of producing a purified ester-substituted phenol stream from a melt transesterification reaction byproduct stream, the method comprising the sequential steps of:
   (a) obtaining from a melt transesterification reaction a byproduct stream comprising a residual ester-substituted diaryl carbonate, an ester-substituted phenol, a residual melt transesterification catalyst, and a catalyst degradation product,
      wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and
      wherein the catalyst degradation product comprises a trialkyl phosphine, a trialkyl amine, or both, (b) introducing the byproduct stream to a first rectification column operating under conditions to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and (c) introducing the light recycle stream to a second rectification column operating under conditions to separate catalyst degradation product from ester-substituted phenol, thereby creating a catalyst degradation product stream and a purified ester-substituted phenol stream, wherein the ester-substituted phenol stream has less than 1.00 ppm catalyst degradation product present.

12. The method of claim 11, wherein the light recycle stream further comprises residual melt transesterification catalyst in an amount of less than 0.10 ppm.

13. The method of claim 1, wherein the purified ester-substituted phenol stream phenol comprises less than 0.10 ppm of catalyst degradation product.

14. The method of claim 11, wherein:
the tetraalkyl phosphonium hydroxide comprises tetramethyl phosphonium hydroxide, diethyldimethyl phosphonium hydroxide, or both,
the tetraalkyl ammonium hydroxide comprises tetramethyl ammonium hydroxide, diethyldimethyl ammonium hydroxide, or both, and
the catalyst degradation product is trimethyl phosphine, diethylmethyl phosphine, dimethylethyl phosphine, trimethyl amine, diethylmethyl amine, dimethylethyl amine, or any combination thereof.

15. The method of claim 11, wherein the method further comprises the step of:
(d) introducing the purified ester-substituted phenol stream to a single-stage separator.

16. The method of claim 11, wherein the byproduct stream further comprises a residual dihydroxy monomer compound and a dihydroxy monomer degradation product, step (b) is performed to create a light recycle stream further comprising dihydroxy monomer degradation product and a heavy recycle stream further comprising residual dihydroxy monomer compound, and step (c) is performed to produce a catalyst degradation product stream further comprising dihydroxy monomer degradation product and a purified ester-substituted phenol stream, wherein the ester-substituted phenol stream has less than 1.00 ppm catalyst degradation product present and less than 100 ppm dihydroxy monomer degradation product present.

17. A method of producing an ester-substituted diaryl carbonate from a purified ester-substituted phenol stream from a melt transesterification reaction byproduct stream, the method comprising the sequential steps of:
(a) obtaining from a melt transesterification reaction a byproduct stream comprising a residual ester-substituted diaryl carbonate, an ester-substituted phenol, a residual melt transesterification catalyst, and a catalyst degradation product,
wherein the melt transesterification catalyst comprises a tetraalkyl phosphonium hydroxide, a tetraalkyl ammonium hydroxide, or both, wherein at least one alkyl group of the tetraalkyl phosphonium hydroxide, the tetraalkyl ammonium hydroxide, or both, is a methyl group, and
wherein the catalyst degradation product comprises a trialkyl phosphine, a trialkyl amine, or both,
(b) introducing the byproduct stream to a first rectification column operating under conditions to separate ester-substituted phenol and catalyst degradation product from residual ester-substituted diaryl carbonate and residual melt transesterification catalyst, thereby creating a light recycle stream comprising ester-substituted phenol and catalyst degradation product and a heavy recycle stream comprising residual ester-substituted diaryl carbonate and residual melt transesterification catalyst, and
(c) introducing the light recycle stream to a second rectification column operating under conditions to separate catalyst degradation product from ester-substituted phenol, thereby creating a catalyst degradation product stream and a purified ester-substituted phenol stream, wherein the ester-substituted phenol stream has less than 1.00 ppm catalyst degradation product present,
(d) contacting the ester-substituted phenol stream with phosgene under conditions sufficient to form ester-substituted diaryl carbonate,
thereby forming ester-substituted diaryl carbonate.

18. The method of claim 17, wherein the light recycle stream further comprises melt transesterification catalyst in an amount of less than 0.10 ppm.

19. The method of claim 17, wherein the purified ester-substituted phenol stream comprises less than 0.10 ppm of catalyst degradation product.

20. The method of claim 17, wherein:
the tetraalkyl phosphonium hydroxide comprises tetramethyl phosphonium hydroxide, diethyldimethyl phosphonium hydroxide, or both,
the tetraalkyl ammonium hydroxide comprises tetramethyl ammonium hydroxide, diethyldimethyl ammonium hydroxide, or both, and
the catalyst degradation product is trimethyl phosphine, diethylmethyl phosphine, dimethylethyl phosphine, trimethyl amine, diethylmethyl amine, dimethylethyl amine, or any combination thereof.

* * * * *

UNITED STATES PATENT AND TRADEMARK OFFICE
CERTIFICATE OF CORRECTION

| | | |
|---|---|---|
| PATENT NO. | : 8,034,967 B2 | |
| APPLICATION NO. | : 11/948063 | |
| DATED | : October 11, 2011 | |
| INVENTOR(S) | : Belfadel et al. | |

It is certified that error appears in the above-identified patent and that said Letters Patent is hereby corrected as shown below:

Column 27, Claim 13, Lines 22 - 24 should read: -- The method of claim 11, wherein the purified ester-substituted phenol stream comprises less than 0.10 ppm of catalyst degradation product. --

Signed and Sealed this
Sixth Day of December, 2011

David J. Kappos
*Director of the United States Patent and Trademark Office*